(12) United States Patent
Conner et al.

(10) Patent No.: US 9,205,929 B2
(45) Date of Patent: Dec. 8, 2015

(54) SYSTEM AND METHOD FOR PROVIDING MODEL-BASED ALERTING OF SPATIAL DISORIENTATION TO A PILOT

(71) Applicant: HONEYWELL INTERNATIONAL INC., Morristown, NJ (US)

(72) Inventors: Kevin J Conner, Kent, WA (US); Santosh Mathan, Seattle, WA (US); Steve Johnson, North Bend, WA (US)

(73) Assignee: Honeywell International Inc., Morris Plains, NJ (US)

(*) Notice: Subject to any disclaimer, the term of this patent is extended or adjusted under 35 U.S.C. 154(b) by 181 days.

(21) Appl. No.: 13/943,549

(22) Filed: Jul. 16, 2013

(65) Prior Publication Data
US 2015/0022380 A1 Jan. 22, 2015

(51) Int. Cl.
| G08B 23/00 | (2006.01) |
| B64D 45/00 | (2006.01) |
| A61B 5/00 | (2006.01) |
| G01C 23/00 | (2006.01) |
| G01C 21/00 | (2006.01) |
| G06F 7/70 | (2006.01) |

(52) U.S. Cl.
CPC . *B64D 45/00* (2013.01); *A61B 5/00* (2013.01); *A61B 5/4023* (2013.01); *A61B 2503/22* (2013.01); *B64D 2045/004* (2013.01)

(58) Field of Classification Search
USPC .............................. 340/967, 980, 963; 701/14
See application file for complete search history.

(56) References Cited

U.S. PATENT DOCUMENTS

| 5,629,848 A | 5/1997 | Repperger et al. | |
| 6,054,937 A * | 4/2000 | Von Viebahn | G01C 23/005 340/961 |
| 8,063,798 B2 | 11/2011 | Cernasov et al. | |
| 2002/0099528 A1 * | 7/2002 | Hett | G01C 23/005 703/13 |
| 2003/0132860 A1 * | 7/2003 | Feyereisen | G01C 23/00 340/973 |
| 2006/0253001 A1 | 11/2006 | Small et al. | |
| 2011/0205090 A1 * | 8/2011 | Marstall | G01C 23/005 340/975 |
| 2011/0282130 A1 | 11/2011 | Krueger | |

OTHER PUBLICATIONS

EP Search Report for Application No. 14166451.6 dated Dec. 12, 2014.
EP Examination Report for Application No. 14166451.6 dated Jan. 8, 2015.
Holly J.E., et al.; Spatial Disorientation in Gondola Centrifuges Predicted by the Form of Motion as a Whole in 3-D; Aviation, Space, and Environmental Medicine, vol. 80, No. 2, Feb. 2009.
Macneilage, P., PhD., Washington University, 2009; Psychophysics and Modeling of Spatial Orientation Perception (Postdoctoral Fellowship); National Space Biomedical Research Institute.
McGrath, B.J., et al.; Analysis of Spatial Disorientation Mishaps in the US Navy; Apr. 15-17, 2002, published in RTO-MP-086.
EP Examination for EP 14166451.6-1557; dated Sep. 9, 2015.

* cited by examiner

*Primary Examiner* — Jack K Wang
(74) *Attorney, Agent, or Firm* — Ingrassia Fisher & Lorenz, P.C.

(57) ABSTRACT

A system and method monitor aircraft state parameters, for example, aircraft movement and flight parameters, applies those inputs to a spatial disorientation model, and makes a prediction of when pilot may become spatially disoriented. Once the system predicts a potentially disoriented pilot, the sensitivity for alerting the pilot to conditions exceeding a threshold can be increased and allow for an earlier alert to mitigate the possibility of an incorrect control input.

18 Claims, 4 Drawing Sheets

SYSTEM AND METHOD FOR PROVIDING MODEL-BASED ALERTING OF SPATIAL DISORIENTATION TO A PILOT

STATEMENT REGARDING FEDERALLY SPONSORED RESEARCH OR DEVELOPMENT

This invention was made with Government support under NNL13AA00C awarded NASA. The Government has certain rights in the invention.

TECHNICAL FIELD

The exemplary embodiments described herein generally relate to recognizing spatial disorientation and, more particularly, to providing model based alerting to a pilot of the possibility of spatial disorientation and to a pilot already disoriented.

BACKGROUND

Research indicates that aircraft loss-of-control incidents represent the leading cause of fatalities both in air transport and general aviation operations. While the precipitating causes of vehicle upsets are diverse, incident findings suggest that a flight crew can become disoriented and incapable of responding to unusual attitudes and other envelope excursions. Several aspects of the interaction between the flight environment and the human perceptual system contribute to these difficulties: 1) the aircraft generates forces that can be misinterpreted as the effect of gravity, making it difficult to establish vertical orientation; 2) pitch and roll maneuvers often do not generate a sense of tilt with respect to gravity; 3) accelerations can induce an inaccurate sense of tilt; and 4) sustained rotations can impede the ability to sense angular motion. The effects of these aspects noted above may be more pronounced in environments where visual cues are deficient. Under circumstances when many of these elements are present, it may be difficult for a pilot to respond appropriately.

Generally speaking, normal flight may be impacted by vehicle movement and external forces (hazard or disturbance), causing poor situational awareness (distraction), spatial disorientation, and mode confusion, resulting in abnormal attitudes, abnormal trajectory, and loss of aircraft control, for example, a stall.

The human vestibular system, which contributes to balance and to the sense of spatial orientation, is the sensory system that provides the leading contribution regarding movement and sense of balance. The vestibular system comprises two components that detect rotation and translation: the semicircular canal system (three orthogonal semicircular canals), which indicates rotational movements; and the otoliths, which indicate linear accelerations. The vestibular system sends signals primarily to the neural structures that control eye movements, and to the muscles that allows one to sense an upright position. Movement of fluid within the horizontal semicircular canal corresponds to rotation of the head around a vertical axis, for example, the neck when doing a pirouette. The anterior and posterior semicircular canals detect rotation of the head in the sagittal plane, for example, when nodding, and in the frontal plane, for example, when cartwheeling. The movement of fluid pushes on hair cells that transduce the mechanical movement to electrical signals.

Experience from the vestibular system is called equilibrioception. It is mainly used for the sense of balance and for spatial orientation. When the vestibular system is stimulated without any other inputs, one experiences a sense of self-motion. For example, a person in complete darkness and sitting in a chair will feel that he or she has turned to the left if the chair is turned to the left. A person in an elevator, with essentially constant visual input, will feel she is descending as the elevator starts to descend. Although the vestibular system is a relatively fast sense used to generate reflexes to maintain perceptual and postural stability, compared to the other senses of vision, touch and audition, vestibular input is perceived with delay.

Because human senses are believed to be adapted for use on the ground, navigating by sensory input alone during flight can be misleading: sensory input does not always accurately reflect the movement of the aircraft, causing sensory illusions. These illusions can be extremely dangerous for pilots.

Illusions involving the semicircular and somatogyral canals of the vestibular system of the ear occur primarily under conditions of unreliable or unavailable external visual references and result in false sensations of rotation and/or motion. These include the leans, the graveyard spin and spiral, and the Coriolis illusion.

The leans is the most common illusion during flight, and is caused by a sudden return to level flight following a gradual and prolonged turn that went unnoticed by the pilot. The reason a pilot can be unaware of such a gradual turn is that human exposure to a rotational acceleration of 2 degrees per second squared or lower is below the detection threshold of the semicircular canals. Leveling the wings after such a turn may cause an illusion that the aircraft is banking in the opposite direction. In response to such an illusion, a pilot may lean in the direction of the original turn in a corrective attempt to regain the perception of a correct vertical posture.

The graveyard spin is an illusion that can occur to a pilot who enters a spin. For example, a pilot who enters a spin to the left will initially have a sensation of spinning in the same direction. However, if the left spin continues the pilot will have the sensation that the spin is progressively decreasing. At this point, if the pilot applies right rudder to stop the left spin, the pilot will suddenly sense a spin in the opposite direction (to the right).

If the pilot believes that the airplane is spinning to the right, the response will be to apply left rudder to counteract the sensation of a right spin. However, by applying left rudder the pilot will unknowingly re-enter the original left spin. If the pilot cross-checks the turn indicator, he would see the turn needle indicating a left turn while he senses a right turn. This creates a sensory conflict between what the pilot sees on the instruments and what the pilot feels. If the pilot believes the body sensations instead of trusting the instruments, the left spin will continue. If enough altitude is lost before this illusion is recognized and corrective action is not taken, impact with terrain may occur.

The graveyard spiral is more common than the graveyard spin, and it is associated with a return to level flight following a prolonged bank turn. For example, a pilot who enters a banking turn to the left will initially have a sensation of a turn in the same direction. If the left turn continues (for more than about 20 seconds), the pilot will experience the sensation that the airplane is no longer turning to the left. At this point, if the pilot attempts to level the wings this action will produce a sensation that the airplane is turning and banking in the opposite direction (to the right). If the pilot believes the illusion of a right turn (which can be very compelling), he will re-enter the original left turn in an attempt to counteract the sensation of a right turn.

An illusion caused by the coriolis involves the simultaneous stimulation of two semicircular canals and is associated with a sudden tilting (forward or backwards) of the pilot's head while the aircraft is turning. This can occur when tilting the head down (to look at an approach chart or to write on the knee pad), or up (to look at an overhead instrument or switch) or sideways. This can produce an overpowering sensation that the aircraft is rolling, pitching, and yawing all at the same time, which can be compared with the sensation of rolling down a hillside. This illusion can make the pilot quickly become disoriented and lose control of the aircraft.

Somatogravic illusions are caused by linear accelerations. These illusions involving the utricle and the saccule of the vestibular system are most likely to occur under conditions with unreliable or unavailable external visual references.

Accordingly, it is desirable to provide an alert to the pilot when current flight parameters produce conditions where pilot disorientation is likely. Furthermore, other desirable features and characteristics of the exemplary embodiments will become apparent from the subsequent detailed description and the appended claims, taken in conjunction with the accompanying drawings and the foregoing technical field and background.

BRIEF SUMMARY

A system and method are provided for alerting a pilot of the possibility of spatial disorientation.

In an exemplary embodiment, a method of alerting a crewmember of a vehicle of the possible existence of spatial disorientation, comprising sensing a plurality of vehicle state parameters; passing the sensed vehicle state parameters through at least one transfer function associated with a human sensory system in order to estimate perceived vehicle state parameters; comparing the perceived vehicle state parameters with the sensed vehicle state parameters; and alerting the crewmember of the possibility of spatial disorientation if the discrepancy between perceived vehicle state parameters and sensed vehicle state parameters exceed a predetermined threshold.

In another exemplary embodiment, a method of alerting a crewmember of an aircraft of the possible existence of spatial disorientation, comprising sensing at least one aircraft state parameter; estimating a perceived aircraft state parameter from the sensed aircraft state parameter within a computational model associated with a human vestibular system; comparing the sensed aircraft state parameter to the perceived aircraft state parameter within the computational model to provide a compared aircraft state parameter; associating the compared aircraft state parameter with a stored aircraft state parameter known to have previously caused spatial disorientation, the computational model including a predetermined threshold; adjusting the predetermined threshold in view of the association; and alerting the crewmember of the possibility of spatial disorientation if a discrepancy between the actual aircraft state and the perceived aircraft state parameter exceeds the adjusted predetermined threshold.

In yet another exemplary embodiment, an apparatus for alerting a crewmember of a vehicle of the possible existence of spatial disorientation, the system comprising a memory storing a set of transfer functions that characterize the perceived state of the vehicle based on specified inputs; a system configured to provide current aircraft state parameters of the aircraft; a processor configured to compare the current aircraft state parameters with estimates of perceived aircraft state parameters; and an alerting system configured to alert the crewmember if the comparison exceeds a threshold.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely illustrative in nature and is not intended to limit the embodiments of the subject matter or the application and uses of such embodiments. Any implementation described herein as exemplary is not necessarily to be construed as preferred or advantageous over other implementations. Furthermore, there is no intention to be bound by any expressed or implied theory presented in the preceding technical field, background, brief summary, or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to graphics and image processing, navigation, flight planning, aircraft controls, aircraft data communication systems, and other functional aspects of certain systems and subsystems (and the individual operating components thereof) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

The following description refers to elements or nodes or features being "coupled" together. As used herein, unless expressly stated otherwise, "coupled" means that one element/node/feature is directly or indirectly joined to (or directly or indirectly communicates with) another element/node/feature, and not necessarily mechanically. Thus, although the drawings may depict one exemplary arrangement of elements, additional intervening elements, devices, features, or components may be present in an embodiment of the depicted subject matter. In addition, certain terminology may also be used in the following description for the purpose of reference only, and thus are not intended to be limiting.

In accordance with the exemplary embodiments, an advisory system provides an alert to the pilot when current flight parameters are associated with conditions that are likely to lead to disorientation of the pilot. The system considers parameters from sensors and avionic systems. The alert may be audio and/or visual.

Figure 1:
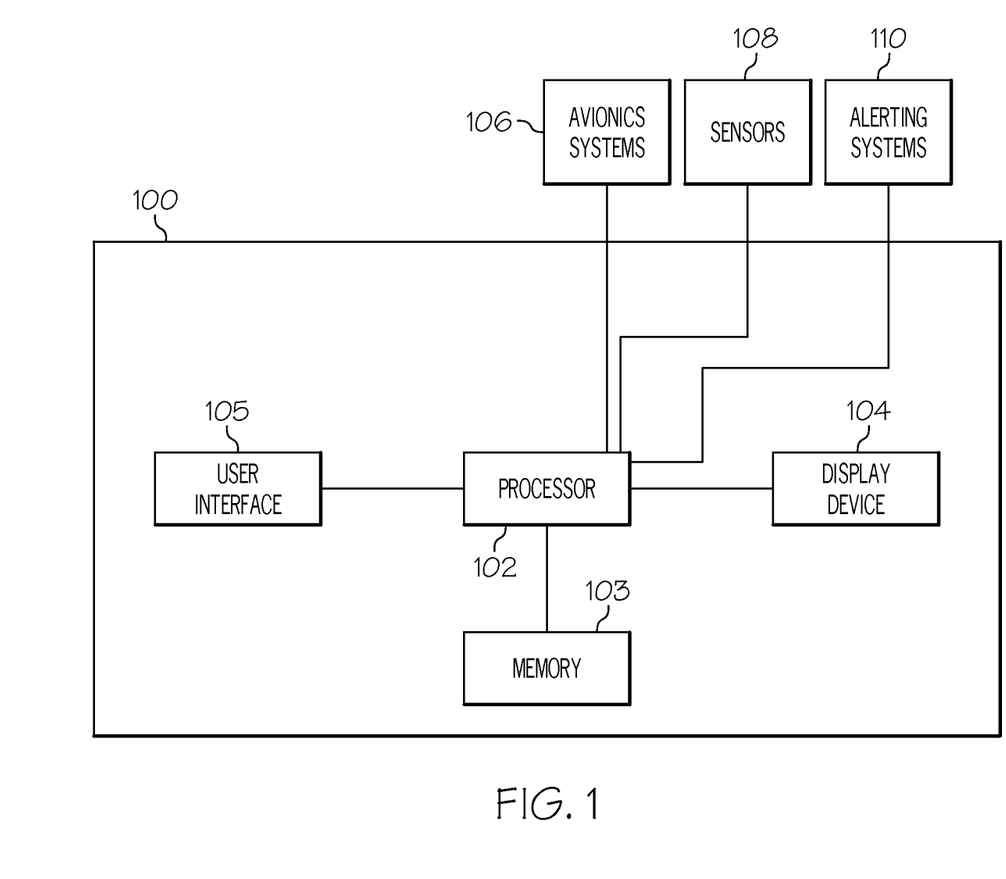
FIG. 1 is a block diagram of a known display system suitable for use in an aircraft in accordance with the exemplary embodiments described herein.

It should be understood that FIG. 1 is a simplified representation of a system 100 for purposes of explanation and ease of description, and FIG. 1 is not intended to limit the application or scope of the subject matter in any way. In practice, the system 100 will include numerous other devices and components for providing additional functions and features, as will be appreciated in the art.

Referring to FIG. 1, an exemplary system 100 is coupled to avionics systems 106, one or more sensors 108, alerting systems 110, and includes a processor 102, a memory 103, an optional display device 104, and a user interface 105. The processor 102 communicates with the memory 103, the display device 104, the user interface 105, the avionics systems 106, the sensors 108, and the alerting systems 110.

The processor 102 may be implemented or realized with a general purpose processor, a content addressable memory, a digital signal processor, an application specific integrated circuit, a field programmable gate array, any suitable programmable logic device, discrete gate or transistor logic, discrete hardware components, or any combination designed to perform the functions described herein. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

The memory 103 may be realized as RAM memory, flash memory, EPROM memory, EEPROM memory, registers, a hard disk, a removable disk, a CD-ROM, or any other form of storage medium known in the art. In this regard, the memory 103 can be coupled to the processor 102 such that the processor 102 can read information from, and write information to, the memory 103. In the alternative, the memory 103 may be integral to the processor 102. In practice, a functional or logical module/component of the display device 104 might be realized using program code that is maintained in the memory 103. The memory 103 can be used to store data utilized to support the operation of the system 100, as will become apparent from the following description.

In accordance with an exemplary embodiment, the display device 104 may be implemented using any one of numerous known displays suitable for rendering textual, graphic, and/or iconic information in a format viewable by the operator. The display device 104 may additionally be implemented as a panel mounted display, a HUD (head-up display) projection, or any one of numerous known technologies. It is additionally noted that the display device 104 may be configured as any one of numerous types of aircraft flight deck displays. For example, it may be configured as a multi-function display, a horizontal situation indicator, or a vertical situation indicator. In the depicted embodiment, however, the display device 104 is configured as a primary flight display (PFD).

The sensor system 108 may be implemented using various types of sensors, systems, and or subsystems, now known or developed in the future, for supplying various types of aircraft state data. The state data may also vary, but preferably include data representative of the geographic position of the aircraft and also other data such as, for example, aircraft speed, heading, altitude, and attitude.

In operation, the system 100 is also configured to process the current flight status data for the host aircraft. In this regard, the sources of flight status data generate, measure, and/or provide different types of data and information related to the operational status of the host aircraft, the environment in which the host aircraft is operating, flight parameters, and the like. In practice, the sources of flight status data may be realized using line replaceable units (LRUs), transducers, accelerometers, instruments, sensors, and other well-known devices. The data provided by the sources of flight status data may include, without limitation: airspeed data; ground speed data; altitude data; attitude data, including pitch data and roll data; yaw data; time/date information; and heading information. The system 100 is suitably designed to process data obtained from the sources of flight status data in the manner described in more detail herein. In particular, the system 100 can use the flight status data of the host aircraft when rendering the display.

The number and type of avionics systems 106 (or subsystems) may also vary, but typically include, for example, a global positioning system (GPS) receiver and an inertial navigation system (INS) receiver (not shown). The other avionics receivers may include, for example, a terrain avoidance and warning system (TAWS), a flight director, and a navigation computer.

Prior research extending as far back as the 1960s has attempted to model the mapping between environmental stimuli (including inertial forces, visual flow, and tactile cues) and a perceived state. Mathematical transfer functions have been developed on the basis of psychophysical research to provide a formal and precise description of the specific ways in which input stimuli may be transformed to perceived motion state. These models have been used to advance the understanding of the human vestibular system and factors contributing to spatial disorientation. In accordance with the embodiments described herein, sensed data is used in conjunction with these transfer functions in real time to estimate and alert the pilot to the likelihood of spatial disorientation. Spatial disorientation is defined herein as an erroneous sense of one's position and/or motion relative to the plane of the earth's surface, which stems from the incorrect perception in magnitude and direction of any of the aircraft control and performance flight parameters. Loss of energy situational awareness is defined herein as a special case of spatial disorientation that is tied to aircraft energy management. These functions are used as the basis for an alerting system that is sensitive to pilot perceptual estimation.

Numerous aircraft flight parameters generate forces that can be misinterpreted as the effect of gravity, especially when visual cues are deficient, making it difficult for a pilot to maintain vertical orientation. For example, pitch and roll maneuvers often do not generate a sense of tilt with respect to gravity; accelerations can induce an inaccurate sense of tilt; and sustained rotations can impede the ability to sense angular motion. By monitoring the vehicle movement and flight parameters and applying those inputs to a spatial disorientation model, a prediction is made of when the operator may become spatially disoriented. Once the system predicts a potentially disoriented pilot, the sensitivity for alerting the pilot to conditions exceeding a threshold can be increased. This increase in sensitivity can be applied such that only the direction of likely inappropriate control will be increased. For example, the bank angle alert could be adjusted from the normal +/−35 degrees to +/−25 based on the direction of the turn. This would allow for an earlier alert to the incorrect control input.

The three axis data for orientation, velocity, and acceleration are applied to a model of the human vestibular system. This model accounts for the dampening out of stimuli that lead to spatial disorientation. Basically, the vestibular system detects changes and not absolute inputs. From this model it is possible to predict the onset of spatial disorientation. Computational modeling provides integration of disparate experimental findings, provides the ability to assess unforeseen interactions, makes verifiable predictions, and can be revised and updated based on new knowledge.

The type of spatial disorientation may also be determined. Examples of the types of spatial disorientation include, for example, somatogravic illusion. From this, alerting algorithms for control exceeding a threshold are adjusted. Spatial disorientation alerts may be provided, for example, in the plus and minus direction for pitch, roll, and yaw. In a first exemplary embodiment, the bank angle alert is biased to early detection in the direction the model predicts an incorrect control input from a spatially disoriented pilot would be expected. In a second exemplary embodiment, the acceleration of a takeoff would lead to a prediction of over control of pitch into a negative pitch condition. An alert could then be generated for excessive pitch down control inputs.

Figure 2:
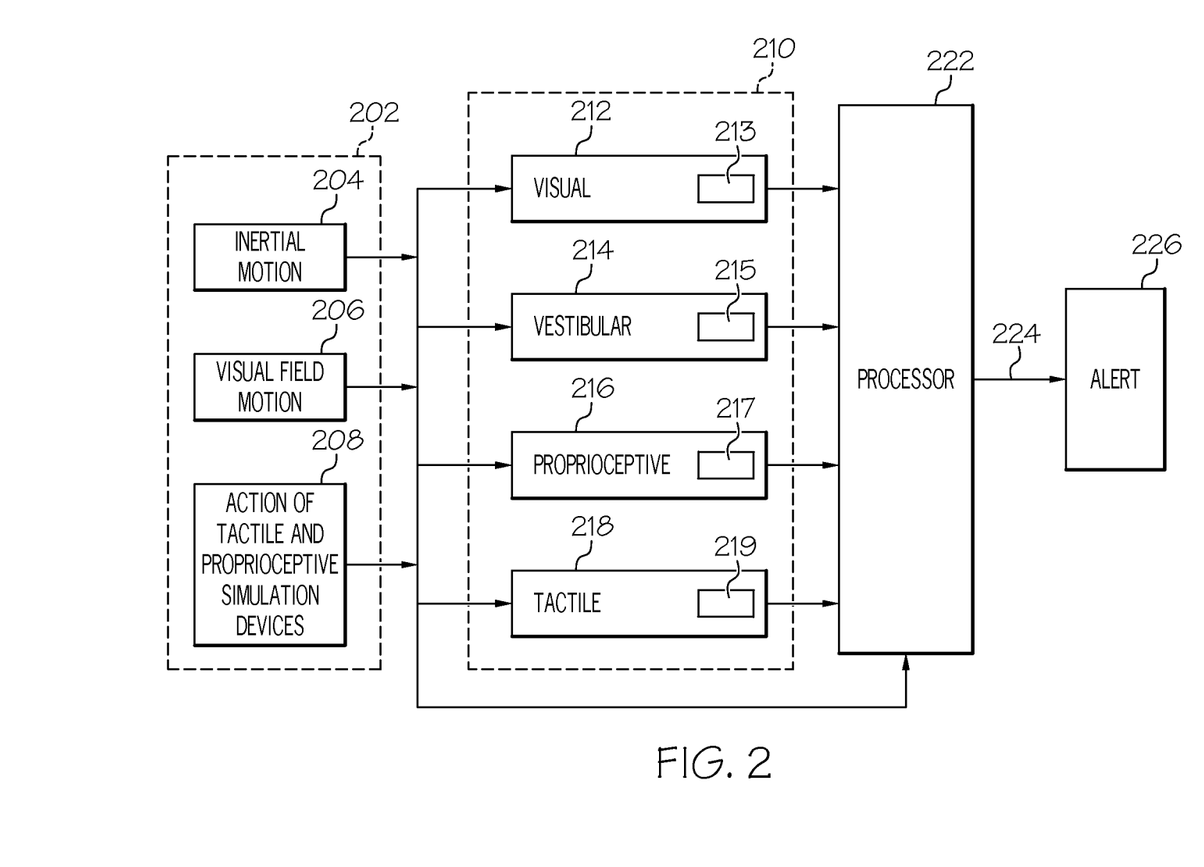
FIG. 2 is a schematic of parameter interactions in accordance with an exemplary embodiment.

More specifically and in accordance with an exemplary embodiment (FIG. 2), aircraft state parameters 202 includes inertial motion 204, visual field motion 206, and action of tactile and proprioceptive stimulation devices 208. Examples of inertial motion 204 include movement of the aircraft due to movement of aircraft controls, wind, and turbulence. The visual field motion 206 may be, for example, viewing a changing background of clouds in relation to the cockpit window frame. An example of action of tactile and proprioceptive stimulation devices 208 is the force between the seat and the body during a turn. These aircraft state parameters 202 are applied to sensor models 210, including a visual model 212, a vestibular model 214, a proprioceptive model 216, and a tactile model 218, each including transfer functions 213, 215, 217, and 219, respectively. Outputs of each of the sensor models 210 are applied to a processor 222 for comparison with outputs from the aircraft state parameters 202 for estimating motion and orientation perceptions of the pilot. When these motion and orientation perceptions exceed a threshold, at least two things may occur. The sensitivity for providing the alert (threshold) may be increased in the direction of disorientation, and a signal 224 may be provided to an alert device 226. The alert may be aural or visual, for example. Some alert systems may be augmented (enhanced) by providing data about the type, direction, and level of the special disorientation. For example, data could be provided to an existing bank angle warning system to adjust the alert threshold in the direction of the disorientation.

Aural alerts play an important role in resolving possible ambiguities associated with visual corrective cues by presenting a redundant verbal message. An aural annunciation of the required corrective action may be included in the exemplary embodiments. In one exemplary embodiment, an aural corrective guidance message is provided, for example, ("ROLL LEFT" (or right); "TO LEVEL! TO LEVEL!"), to the current excessive bank alert ("BANK ANGLE! BANK ANGLE!"). An aural alert may also be provided, for example, to pitch up or pitch down if the improper pitch caused by disorientation is in the vertical direction. Besides communicating corrective action, aural warnings can also help in situations where a pilot may not be visually attending a critical flight parameter.

Figure 3:
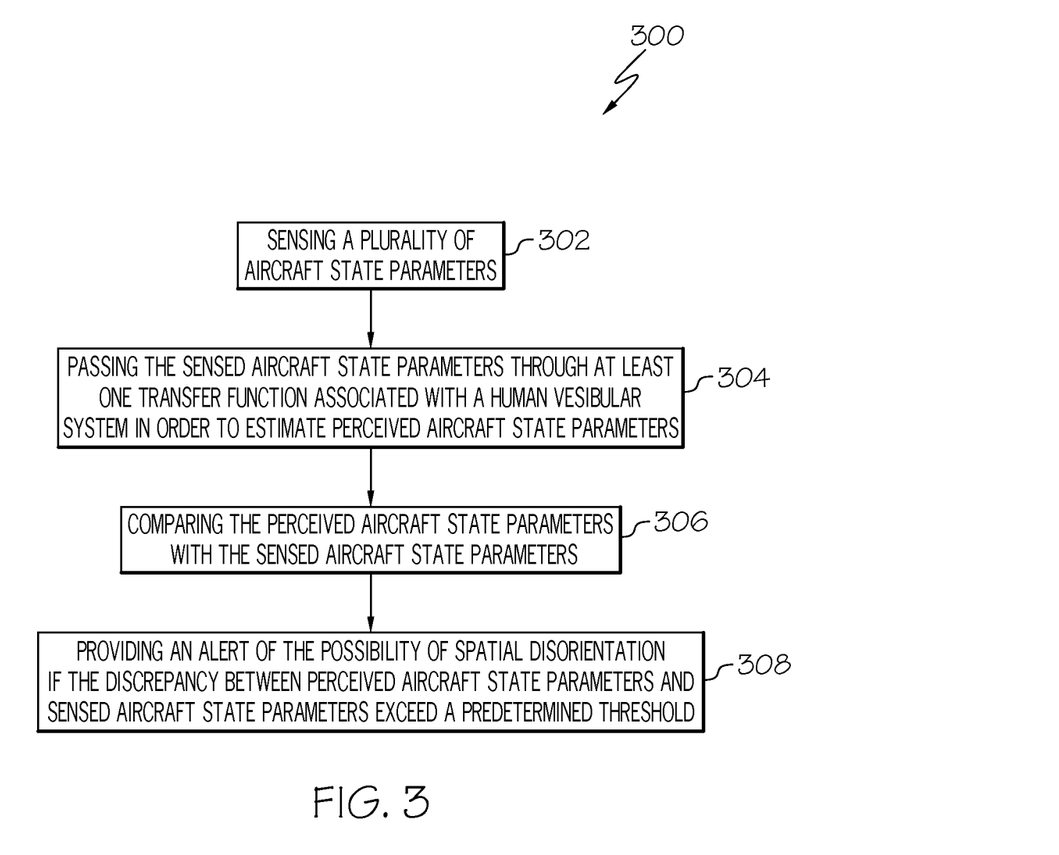
FIGS. 3 and 4 are flow diagrams of exemplary methods suitable for use with the display system of FIG. 1 in accordance with the exemplary embodiments.

FIG. 3 is a flow chart that illustrates an exemplary embodiment of a method 300 suitable for use with a flight deck display system 100. Method 300 represents one implementation of a method for displaying aircraft approaches or departures on an onboard display of a host aircraft. The various tasks performed in connection with method 300 may be performed by software, hardware, firmware, or any combination thereof. For illustrative purposes, the following description of method 300 may refer to elements mentioned above in connection with the preceding FIGS. In practice, portions of method 300 may be performed by different elements of the described system, e.g., a processor, a display element. It should be appreciated that method 300 may include any number of additional or alternative tasks, the tasks shown in FIG. 3 need not be performed in the illustrated order, and method 300 may be incorporated into a more comprehensive procedure or method having additional functionality not described in detail herein. Moreover, one or more of the tasks shown in FIG. 3 could be omitted from an embodiment of the method 300 as long as the intended overall functionality remains intact.

In accordance with the exemplary method of FIG. 3, a method of alerting a crewmember of a vehicle, e.g., an aircraft, of the possible existence of spatial disorientation includes sensing 302 a plurality of aircraft state parameters, passing 304 the sensed aircraft state parameters through at least one transfer function associated with a human vestibular system in order to estimate perceived aircraft state parameters, comparing 306 the perceived aircraft state parameters with the sensed aircraft state parameters; and alerting 308 the crewmember of the possibility of spatial disorientation if the discrepancy between perceived aircraft state parameters and sensed aircraft state parameters exceed a predetermined threshold.

Figure 4:
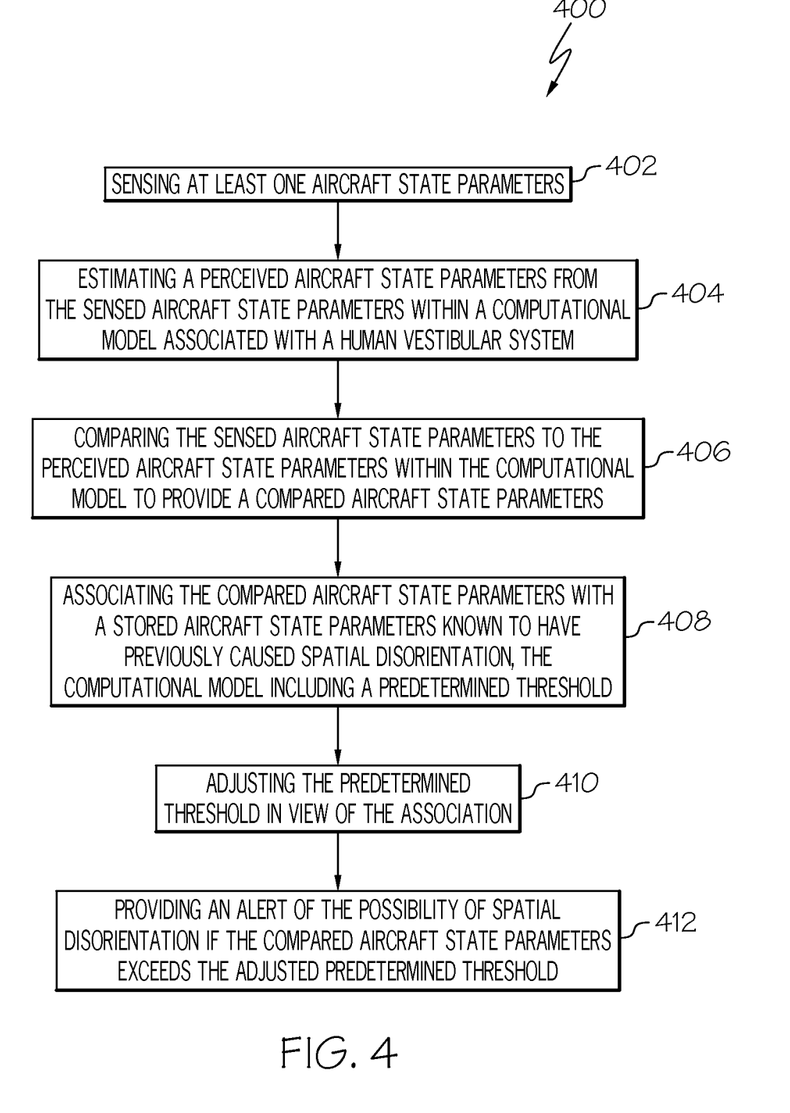

In accordance with the exemplary method of FIG. 4, a method of alerting a crewmember of the possible existence of spatial disorientation includes sensing 402 at least one aircraft state parameter, estimating 404 a perceived one aircraft state parameter from the sensed one aircraft state parameter within a computational model associated with a human vesibular system, comparing 406 the sensed one aircraft state parameter to the perceived one aircraft state parameter within the computational model to provide a compared one aircraft state parameter, associating 408 the compared one aircraft state parameter with a stored one aircraft state parameter known to have previously caused spatial disorientation, the computational model including a predetermined threshold, adjusting 410 the predetermined threshold in view of the association; and alerting 412 the crewmember of the possibility of spatial disorientation if a discrepancy between the actual aircraft state and the perceived aircraft state parameter exceeds the adjusted predetermined threshold.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A method of alerting a crewmember of a vehicle of the possible existence of spatial disorientation, comprising:
   sensing a plurality of vehicle state parameters, wherein vehicle state parameters include input from tactile and proprioceptive simulation devices;
   passing one of the plurality of sensed vehicle state parameters through a transfer function associated with a human sensory system in order to estimate a respective perceived vehicle state parameter;
   comparing the estimated perceived vehicle state parameter with the one of the plurality of sensed vehicle state parameters;
   determining whether the estimated perceived vehicle state parameter exceeds a predetermined threshold;
   increasing a sensitivity of an alert when it is determined that the estimated perceived vehicle state parameter exceeds the predetermined threshold; and
   alerting the crewmember of the possibility of spatial disorientation when it is determined that the estimated perceived vehicle state parameter exceeds the predetermined threshold.

2. The method of claim 1 wherein the estimating of vehicle state parameters comprises:
   estimating using a computational model.

3. The method of claim 1 wherein the passing step comprises:
   passing the one of the plurality of the sensed vehicle state parameters through a transfer function associated with a human vestibular system.

4. The method of claim 3 wherein the vehicle is an aircraft and the sensing further comprises:
   sensing a plurality of flight parameters.

5. The method of claim 3 wherein the predetermined threshold comprises:
   one of a degree of bank of the vehicle and a degree of pitch by the vehicle.

6. The method of claim 1 wherein the passing step comprises:
   passing the one of the plurality of the sensed vehicle state parameters through a transfer function associated with at least one of a human visual, proprioceptive, or tactile system.

7. A method of alerting a crewmember of an aircraft of the possible existence of spatial disorientation, comprising:
   sensing an aircraft state parameter, wherein aircraft state parameters include input from tactile and proprioceptive simulation devices;
   estimating a perceived aircraft state parameter from the sensed aircraft state parameter within a computational model associated with a human vestibular system, the computational model including a predetermined threshold;
   comparing the sensed aircraft state parameter to the estimated perceived aircraft state parameter within the computational model to provide a compared aircraft state parameter;
   associating the compared aircraft state parameter with a stored aircraft state parameter known to have previously caused spatial disorientation;
   adjusting the predetermined threshold in view of the association;
   determining whether the estimated perceived aircraft state parameter exceeds the adjusted predetermined threshold; and
   alerting the crewmember of the possibility of spatial disorientation when it is determined that the estimated perceived aircraft state parameter exceeds the adjusted predetermined threshold.

8. The method of claim 7 wherein the sensing further comprises sensing a plurality of flight parameters.

9. The method of claim 7 wherein the predetermined threshold comprises:
   a degree of bank of the aircraft.

10. The method of claim 7 wherein the predetermined threshold comprises:
    a degree of pitch of the aircraft.

11. The method of claim 7 wherein the estimating of the aircraft state parameter comprises:
    estimating using a computational model.

12. The method of claim 7 further comprising:
    modifying the predetermined threshold in accordance with the comparison of the perceived vehicle state parameters with the sensed vehicle state parameters.

13. An apparatus for alerting a crewmember of a vehicle of the possible existence of spatial disorientation, the system comprising:
    a memory storing a set of transfer functions that characterize the perceived state of the vehicle based on specified inputs;
    a system configured to provide current vehicle state parameters of the vehicle, wherein vehicle state parameters include input from tactile and proprioceptive simulation devices;
    a processor configured to:
      receive a current vehicle state parameter,
      estimate a respective perceived vehicle state parameter,
      compare the current vehicle state parameter with the estimated perceived vehicle state parameter,
      retrieve an associated predetermined threshold; and
      determine whether the estimated perceived vehicle state parameter exceeds the predetermined threshold;
      increase a sensitivity of an alert when it is determined that the estimated perceived vehicle state parameter exceeds the predetermined threshold; and
      command an alerting system coupled to the processor and configured to alert the crewmember to generate an alert when it is determined that the estimated perceived aircraft state parameter exceeds the predetermined threshold.

14. The system of claim 13 wherein the vehicle is an aircraft and the system is further configured to:
    provide a plurality of flight parameters as the current aircraft state parameters.

15. The system of claim 13 wherein the threshold comprises:
    one of a degree of bank of the vehicle and a degree of pitch of the vehicle.

16. The system of claim 13 wherein the processor is configured to:
    provide a computational model.

17. The system of claim 13 wherein the processor is configured to:
    compare the current vehicle state parameters with estimates of perceived vehicle state parameters based on the human vestibular system.

18. The system of claim 13 wherein the processor is further configured to:
    compare the current vehicle state parameters with estimates of perceived vehicle state parameters based on at least one of the human systems comprising human visual, proprioceptive, or tactile system.

* * * * *